United States Patent [19]

Meguro et al.

[11] Patent Number: 4,640,943
[45] Date of Patent: Feb. 3, 1987

[54] SURFACE MODIFIER FOR INORGANIC SUBSTANCES

[75] Inventors: Kenjiro Meguro, Tokyo; Koichiro Sagawa; Hirofumi Yokota, both of Kawasaki; Masahiro Takehara, Fujisawa, all of Japan

[73] Assignee: Ajinomoto Co., Inc., Tokyo, Japan

[21] Appl. No.: 653,024

[22] Filed: Sep. 21, 1984

[30] Foreign Application Priority Data

Sep. 22, 1983 [JP] Japan .................. 58-175708
Sep. 22, 1983 [JP] Japan .................. 58-175709
Jun. 26, 1984 [JP] Japan .................. 59-131781

[51] Int. Cl.$^4$ .................. C08L 83/00; C04B 14/00; A61K 7/035
[52] U.S. Cl. .................. 523/200; 106/308 N; 106/308 F; 424/69
[58] Field of Search .................. 106/308 N, 308 F; 252/546; 260/404.5, 404.5 A; 424/69; 523/200

[56] References Cited

U.S. PATENT DOCUMENTS

| 2,063,987 | 12/1936 | Dreyfus | 260/404.5 |
| 2,852,406 | 9/1958 | Riegler | 106/308 N |
| 3,148,026 | 9/1964 | Roderburg | 106/308 N |
| 3,897,466 | 7/1975 | Takizawa et al. | 260/404.5 A |
| 4,126,628 | 11/1978 | Paquet | 260/404.5 A |
| 4,478,734 | 10/1984 | Ogino et al. | 260/404.5 |

OTHER PUBLICATIONS

Bulletin of the Chemical Society of Japan, vol. 56, No. 9, last page, dated Sep. 15, 1983.
"Surface Treatment of Inorganic Pigments by N-Acyllysine" Esumi et al., Bull Chem Soc Japan, 56, 2569-2571 (Sep. 1983).

Primary Examiner—Theodore Morris
Attorney, Agent, or Firm—Oblon, Fisher, Spivak, McClelland, & Maier

[57] ABSTRACT

An inorganic composition of improved characteristics comprising at least one particulate inorganic substance whose surface is modified by an N-acylated basic amino acid.

16 Claims, 15 Drawing Figures

SURFACE MODIFIER FOR INORGANIC SUBSTANCES

BACKGROUND OF THE INVENTION

1. Field of the Invention

The present invention relates to particulate inorganic materials whose surfaces have been modified by a surface modifying organic material.

2. Description of the Prior Art

In recent years, in various fields of technology such as paint formulation, resins, and electronics, composite materials prepared by mixing and dispersing such inorganic fillers as bentonite, kaolin, diatomaceous earth, light-weight silicic anhydride, calcium carbonate, titanium dioxide, mica, calcium secondary phosphate, alumina, barium sulfate, zinc oxide, yellow iron oxide, red iron oxide, black iron oxide, ultramarine, chromium hydroxide, chromium oxide, montmorillonite, asbestos, talc, silica, ferrite, metallic fibers, and glass fibers in such organic media as resins and paints have come to be used for the purpose of imparting strength and toughness to the composite materials, for enhancing the resistance of the composite materials to heat and weather conditions, for improving color tone and viscosity, for reducing costs by adulteration of the composition, and for conferring electroconductivity to the composite material as a newly acquired function.

The surface of such inorganic substances are generally covered with polar groups such as hydroxyl groups and because of this fact adsorb moisture. The surfaces therefore do not have much affinity for oils and are liable to be wetted by water. Thus, these inorganic substances cannot be uniformly dispersed in organic media such as paints and resins without entailing difficulty.

On the other hand, in the area of cosmetic formulations, inorganic powders and pigments have been used as coloring agents and fillers in such formulations. However, these inorganic powders present disadvantages such as that titanium dioxide, and the like are very hydrophilic and are only difficulty compounded with oily base materials although they have a good masking power. Further, while the pH of the skin is between 5 and 6, kaolin has a markedly high pH and strong surface activity, and therefore there are significant restrictions on its use in cosmetic formulations from the viewpoint of safety.

The conventional inorganic pigments are unsatisfactory because they are poorly compatible with and poorly dispersed in the oily base of a cosmetic formulation, because the surfaces thereof are hydrophilic so that homogeneous cosmetics having smooth texture are obtained only with difficulty. In addition, when the inorganic pigments are spread over the skin, the disadvantages which are encountered are that adherence to the skin is insufficient and the cosmetic easily fall off the skin surface. Further, problems are the safety and stability of the cosmetic because the inorganic pigments have strong surface activity and for this reason, accelerate the oxidation of oily components used in cosmetics to peroxides which irritate the skin or generate aromatic compounds.

In view of these circumstances, various method of surface modification have been proposed for the purpose of improving the wettability, enhancing the dispersibility, repressing the surface activity, curbing the skin-irritating property of organic substances, and promoting the stability of coexisting medicines and perfumes.

In the past various surface modifiers have been used for the purpose of improving the wettability and enhancing the dispersibility of such inorganic fillers. Examples of surface modifiers which have been used in the past include surface active agents such as dodecyl sulfuric ester salts, alkylbenzene sulfonates, fatty acid salts, dialkyl sulfosuccinic ester salts, polyoxyethylene alkyl ethers, glycerin fatty acid esters, polyoxyethylene sorbitan fatty esters, quaternary ammonium salts, lecithin, and alkyl bentaine; polymers such as polystyrene, polypropylene, polyesters, styrene-methacrylic acid type copolymers, styrene-acrylic acid type copolymers, polytetrafluoroethylene, polychlorotrifluoroethylene, polyethylenetetrafluoroethylene type copolymers, polyaspartic acid, polyglutamic acid, and polyglutamic acid-γ-methyl esters; and modifiers such as silane coupling agents and alcohols.

The inorganic surface modifiers which are used are required to possess certain characteristic properties, which are (1) the ability to manifest a high dispersing effect at low application rates, (2) the ability to impart strong adsorbancy to the surface of a filler enough to avoid easy separation from treated boundary, and (3) extensive adaptability to various fillers.

Surface active agents such as zinc stearate which are used in some of the method of surface modification of inorganic substances described above are widely used in the field of paints and resins. It is known that when they are used at low application rates, they are not sufficiently effective in improving the dispersibility of the inorganic filler and, when they are used at excessively high rates, they have the disadvantage of causing the phenomenon of bluing during the processing of resins and degrading the water-repellency and weatherability of end products.

When the surface modification of a filler is attempted with polymers such as polystyrene, there is the possibility that, depending on the kind of organic solvent used as a dispersant, a polymer coat formed on the surface of an inorganic substance will swell or dissolve and separate from the surface. When the inorganic substance with such a polymer coat is used in paints, it imposes the problem of limiting the type of solvent which can be used in the paint.

When silane type coupling agents are used, they exhibit an excellent effect of modifying silicon-containing inorganic substances such as glass and silica because the molecules of the silane type coupling agents react with the surface functional groups and form strongly adsorbent films. They, however, fail to manifest this expected effect upon other inorganic fillers such as aluminum trihydrate and exhibit absolutely no effect upon calcium carbonate. This selective failure on the part of silane coupling agent to exhibit any sort of interaction with some fillers indiscriminately is a severe drawback of such silane type coupling agents.

On the other hand, when such inorganic substances are used as a bases for makeup cosmetic articles, they are wetted with perspiration so readily that they cause the peeling of applied coats of makeup. This is a notorious drawback of inorganic substances. It is also known that such inorganic substances as described above have on their surface acid points which exhibit acidity and base points which exhibit basicity and, because of their high surface activity, irritate the skin, accelerate degradation and decomposition of the medicines or perfumes in which they are present or entail other similar problems.

In order to solve such problems, various attempts to compound inorganic pigments, which have undergone surface treatment, have been made in the past. In the cosmetic field, for example, an attempt has been made to improve the adherence of the cosmetic to the skin or to improve the oil absorptivity of the cosmetic by treating the surface of inorganic pigments with silk fibroin (Japanese Published Examined Patent Application 11577/82). However, silk fibroin is not preferred in terms of safety and stability since it easily putrefies, thereby adversely affecting the appearance and fragrance of the cosmetic product. Alternatively, a method is known for inhibiting the surface activity of titanium dioxide by treating the surface with higher alcohol mono-esters of long chain aliphatic acids to render the surface hydrophobic (Japanese Published Examined Patent Application 42167/83). However, titanium dioxide surface-treated with such esters is oily, thereby providing an undesirable texture when spread over the skin. This limits the amount of the modified filler which can be compounded with the cosmetic to about 2%. A method for rendering the surface of an inorganic pigment hydrophobic by treating the surface of inorganic pigments with silicone oil of polysiloxanes is known. However, silicone oil often has a peculiar smell. Further, thus treated inorganic pigments are oily and exhibit poor lubrication properties.

It is also known that inorganic fillers can be treated with such surface active agents as metallic soaps are lecithin in order to modify the surface of powders to avoid the solubilizing effect of such powders in cosmetic makeup formulations. These surface active agents, however, manifest virtually no effect in repressing the activity of inorganic surfaces and fail to solve the problem of degradation of perfumes and coloring matter. They are inevitably required, therefore, to be used in combination with antioxidants or chelating agents, for example. Further, when the inorganic powder which has undergone the surface modification by the use of a polymer such as polystyrene is used in cosmetics, since the surface is no longer hydrophilic, the possibility of the applied coat of makeup being wetted with and dissolved by perspiration is limited. Nevertheless, the residual monomer which is present in the polymer coating may exhibit a toxic effect. Besides, when such polymers are used for surface modification, the treatment inevitably entails use of a highly toxic solvent such as dichloroethane. These factors present important problems in a filed in which safety is an exacting requirement. However, cosmetics which overcome these problems have not yet been formulated.

A need therefore continues to exist for a method of modifying the surfaces of inorganic filler materials in order to improve the compatibility of the filler materials with a variety of different formulations thereby improving the properties of the resultant products.

SUMMARY OF THE INVENTION

Accordingly, one object of the present invention is to provide inorganic filler materials with improved compatibility characteristics for use in the formulation of a variety of different products.

Another object of the invention is to provide inorganic filler materials of modified surface characteristics which are suitable for blending with cosmetics, paints and resin.

Briefly, these objects and other objects of the present invention as hereinafter will become more readily apparent can be attained by modifying the surface of inorganic materials with an N-acylated basic amino acid.

In one embodiment of the invention the surface of an inorganic filler is modified with at least one N-acyl-lysine selected from the group of compounds having the formulas:

wherein RCO is an aliphatic acyl group of 8 to 22 carbon atoms, and R'CO and R''CO each represent an aliphatic acyl group of 1 to 22 carbon atoms with the proviso that the total number of carbon atoms in both the R'CO and R''CO groups ranges from 9 to 44.

In another embodiment of the invention an inorganic filler is modified with a N-monoacylated basic amino acid acylated with an aliphatic acyl group of 8 to 22 carbon atoms.

In yet another embodiment of the invention an inorganic filler is modified by allowing a particulate inorganic substance to absorb a salt of a basic amino acid with a fatty acid of 8 to 22 carbon atoms, and then subsequently heating the modified substance to a temperature to within the range of 100° to 250° C.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

With regard to the embodiment of the invention in which the N-acyl-lysine compounds are used as the surface modifying agent, it has been discovered that inorganic powders modified with an N-acyl-lysine compound have good dispersive power in paint and resins without detaching the N-acyl-lysine compound from the treated surfaces, because of its low solubility in various solvents such as toluene, squalane, liquid paraffin, alcohol, glycerine and the like, specifically among various acyl-amino acids.

On the other hands, when these inorganic materials are used as a component in makeup cosmetic, it has also been discovered that cosmetics having improved wettability, low skin irritation, excellent adherence to the skin, masking power and absorbability of secretions can be produced.

And it has also been discovered that N-acyl-lysine itself has several good properties as a cosmetic raw material.

The N-acyl-lysine compounds of the present invention can be prepared by a reaction which involves the dropwise addition of fatty acid chlorides in an aqueous alkaline solution of lysine, which is the so-called Schotten-Baumann reaction. In this case, when the amino group at the $\alpha$-position or $\epsilon$-position is protected, the monoacylated compounds of the formulas shown above are prepared. Further, the $N^\epsilon$-acylated compound may also be obtained by heating and dehydrating fatty acid salts of lysine at temperatures of 100° to 250° C. (Japanese Published Examined Patent Application 28610/76). Subsequent to the acylation reaction, a given N-acyl-lysine compound is isolated by subjecting the solid-liquid reaction mixture to a solid-liquid separation technique such as filtration or the like. After decolorizing and purifying, if necessary, the N-acyl-lysine compound is pulverized to the desired particle size using grinders such as a ball mill, a colloid mill, an atomizer or the like to obtain the desired powder.

With respect to the acyl group of the lysine derivative, aliphatic acyl groups having 8 to 22 carbon atoms are generally used. By varying the carbon atom content of the acyl group and the number of acyl groups in a given lysine derivative, it is possible to provide an N-acylated lysine compound having a specific balance of hydrophilic and hydrophobic, smoothness, adherence, and masking power properties.

Suitable examples of the N-acyl-lysine compounds of the present invention include $N^\alpha$-oleoyl-lysine, $N^\alpha$-lauroyl-lysine, $N^\alpha$-myristoyl-lysine, $N^\alpha$-palmitoyl-lysine, $N^\alpha$-stearoyl-lysine, $N^\epsilon$-oleoyl-lysine, $N^\epsilon$-lauroyl-lysine, $N^\epsilon$-myristoyl-lysine, $N^\epsilon$-palmitoyl-lysine, $N^\epsilon$-stearoyl-lysine, $N^\alpha$-lauroyl-$N^\epsilon$-stearoyl-lysine, $N^\alpha$-hexanoyl-$N^\epsilon$-palmitoyl-lysine, $N^\alpha$-$N^\epsilon$-dilauroyl-lysine, and the like and mixtures thereof. These N-acyl-lysines may be employed in either optically active form or as a racemic mixture.

It is known that $N^\epsilon$-acyl-lysines and the metal salts thereof can be used as stabilizers for halogen-containing resins such as polyvinyl chloride, or the like (Japanese Published Unexamined Patent Application 12847/76). However, there is no disclosure in the prior art which suggests the use of lysine derivatives in the preparation of cosmetic formulations, and the use of them as inorganic surface modifiers.

The surface of a given inorganic material can be modified with the present N-acyl-lysine compound by several different methods. One method comprises adding the modifier in its unaltered form to a given filler and comminuting the resultant mixture in a grinder such as a ball mill, an atomizer, or a colloid mill. A second method comprises stirring the modifier in conjunction with the filler in a suitable solvent and then treating the resultant solution to expel the solvent. A third method, which is used in paint and resin, comprises directly adding the modifier to a mixture of an organic medium with the filler and blending the resultant mixture as with hot rolls. The second method is preferred over the other methods because it produces the desired surface modification quite effectively at an extremely low application rate. When this surface modification is used on calcium carbonate, for example, ample surface modification is effectively obtained at a minimal application rate of 0.05% based on the amount of calcium carbonate under treatment.

The N-acyl lysine compounds of the present invention can be used for a very wide variety of inorganic fillers such as calcium carbonate, titanium dioxide, kaolin, talc, silica, ferrite, chromium dioxide, metallic fibers, glass fibers, and asbestos. The surface modified inorganic fillers can be effectively mixed in various organic media such as polyurethane resins, vinyl chloride-vinyl acetate copolymers, epoxy resins, phenol resins, acryl resins, cellulose resins, polyamide resins, and urea resins.

It is known that when conventional inorganic pigments are used in the manufacture of paints, it has been frequently observed that the modifier which adsorbs on the surface of the inorganic pigments dissolves out into the organic solvent to induce coagulation and separation of inorganic pigments and impairs the smooth surface and even the color of the coatings containing the pigment. In contrast, the inorganic pigments treated by the N-acyl lysine compound of the present invention have the advantage that they induce coagulation and separation only sparingly in various organic solvents including ketones such as methylethyl ketone, methylisobutyl ketone, and cyclohexanone; esters such as ethyl acetate, and hydrocarbons such as toluene, and they rarely impair the quality of paints.

As described above, the present N-acyl lysine compounds exhibit excellent properties as surface modifiers. These properties are fully manifested not only when the N-acyl lysine compounds are used by themselves, but also when they are used in combination with other surface modifiers.

When the present N-acyl-lysine compounds are used to modify inorganic fillers which are to be used in cosmetic formulations, because the modifier is composed of natural lysine and fatty acids, the modified fillers are less irritative to the skin and show excellent adsorptability and masking power because the surface modifier contains amido groups similar to skin proteins. In addition, the N-acyl-lysines possess hydrocarbon groups which are hydrophobic groups, and amino groups and carboxyl groups which are hydrophilic groups in the molecule thereof. The balance of the hydrophilic groups and the hydrophobic groups can easily be changed by modifying the number and chain length of the acyl groups to be introduced. Accordingly, the dispersibility of the modified filler in oily base materials or aqueous base materials and absorptability of the filler particles to sweat, secretions, and the like can be controlled, whereby it becomes possible to select a given N-acyl-lysine compound on the basis of its specific physical properties.

The modified inorganic filler or powder of the present invention can be used only or with other powders in the preparation of cosmetics, with satisfactory cosmetic properties being obtained.

Cosmetic formulations in which the surface modified inorganic powder of the present invention can be used include face powders, paste powders, solid powders, body powders, baby powders, antihidrotics, foundations, tooth pastes, eye shadow, rouge and the like. In addition, cosmetic formulations also include those which already contain powders therein.

In another embodiment of the present invention it has been found that when an inorganic pigment treated with a long chain monoacylated lysine, the inorganic pigments so treated provide not only improved dispersibility in and compatibility with oily raw materials, but also greatly improved properties required for cosmetic compositions such as adherence to the skin, safety, stability, texture, and the like. Further similar effects can be obtained not only by cosmetics having inorganic pigments treated with long chain monoacylated lysines compounded therein, but also pigments treated with other long chain monoacylated compounds of basic amino acids, which are ornithine, $\alpha,\gamma$-diaminobutyric acid, arginine and histidine. It has been found that these effects are characteristics which are not observed with cosmetic compositions having non-treated inorganic pigments or inorganic pigments surface-treated by conventional, known techniques compounded therein. That is, this aspect of the present invention relates to cosmetic compositions having compounded therein inorganic pigments surface-treated with N-monoacylated basic amino acids.

Suitable examples of inorganic pigments used in the present invention include talc, kaolin, titanium dioxide, titanium-coated mica, mica, iron oxides, silicic acid, ultramarine, Prussian blue, zinc flowers, clay, precipitated calcium carbonate, and the like. The shape and size of these pigment particles are not particularly limited.

As basic mono acids which can be employed to prepare the present N-monoacylated basic amino acids there are $\alpha,\gamma$-diaminobutyric acid, ornithine, lysine, arginine and histidine. These amino acids may be optically active or in a racemic mixture. The long-chain acyl groups may be saturated or unsaturated, straight or branched aliphatic acyl groups having 8 to 22 carbon atoms. A given basic amino acid may be monoacylated with a single acyl group or several different acyl radicals. Specific examples include 2-ethylhexanoyl, capryloyl, caproyl, lauroyl, myristoyl, palmitoyl, stearoyl, isostearoyl, oleoyl, behenoyl, cocoyl, acyl derived from tallow fatty acids, acyl derived from hydrogenated tallow fatty acids, and the like. The site of the long chain acyl groups on the basic amino acids is at the $\alpha$- or higher positioned amino group, provided that it is limited to the amino group at the $\alpha$-position in arginine and histidine. Specific examples include $N^\epsilon$-2-ethylhexanoyl-lysine, $N^\epsilon$-lauroyl-lysine, $N^\epsilon$-cocoyl-lysine, $N^\epsilon$-palmitoyl-lysine, $N^\epsilon$-isostearoyl-lysine, $N^\epsilon$-hydrogenated tallow fatty acid acyl-lysine, $N^\alpha$-capryloyl-lysine, $N^\alpha$-lauroyl-lysine, $N^\alpha$-myristoyl-lysine, $N^\alpha$-oleoyl-lysine, $N^\alpha$-behenoyl-lysine, $N^\delta$-cocoyl-orinithine, $N^\delta$-stearoyl-ornithine, $N^\delta$-tallow fatty acid acyl-ornithine, $N^\alpha$-2-ethylhexanoyl-ornithine, $N^\alpha$-lauroyl-ornithine, $N^\alpha$-isostearoyl-ornithine, $N^\alpha$-palmitoyl-$\alpha,\gamma$-diaminobutyric acid, $N^\alpha$-tallow fatty acid acyl-$\alpha,\gamma$-diamino-butyric acid, $N^\alpha$-caproyl-arginine, $N^\alpha$-lauroyl-arginine, $N^\alpha$-palmitoyl-arginine, $N^\alpha$-hydrogenated tallow fatty acid acyl-arginine, $N^\alpha$-cocoyl-histidine, $N^\alpha$-isostearoyl-histidine, and the like, but the invention is not limited to these specific compounds.

In treating a given inorganic pigment with the N-monoacylated basic amino acid, any dry or wet procedure can be used.

The dry procedure is simple and effective. The surface of the inorganic pigment can be easily treated either by mixing a finely divided N-mono-acylated basic amino acid powder, i.e., having an average particle size of 0.1 to 10$\mu$, preferably 0.1 to 5$\mu$, with a given inorganic pigment with stirring or by mixing the N-long chain mono-acylated basic amino acid with the inorganic pigment and then co-pulverizing the mixture. Alternatively, the wet procedure can be adopted in order to obtain the treatment effect with a smaller amount of the N-long chain monoacylated basic amino acid. In this case, the N-long chain monoacylated basic amino acids are hardly soluble in water and are hardly soluble in oily raw materials which are conventionally used in the preparation of cosmetics. Accordingly, the quality of the surface of the inorganic pigments can be effectively modified by dissolving the N-long chain monoacylated basic amino acid in organic solvents using calcium chloride as a solubilizing agent, bringing the inorganic pigment into contact with the solution and then washing the mixture with water to remove calcium chloride. Alternatively, a surface treatment effect similar to this can also be obtained by dissolving the N-long chain monoacylated basic amino acid in alkaline water or an aqueous solvent, bringing the inorganic pigment into contact with the solution, neutrallizing the mixture to about a neutral pH, precipitating and adhering the N-long chain monoacylated basic amino acid onto the surface of the pigment, washing the salt formed by neutrallization with water to remove it and then drying the compound obtained.

The cosmetic composition having the present surface treated inorganic pigments compounded therein possesses various advantages that are not observed with cosmetic compositions untreated or treated by conventionally known techniques. That is, (1) the present inorganic pigment exhibits excellent dispersibility in and compatability with oily raw materials, the products are homogeneous and not sandy and have smooth texture; (2) the adherence of the surface treated pigment containing cosmetic to the skin is excellent so that the cosmetic makeup comes off only with difficulty; (3) the surface activity of the inorganic pigment is retarded so that the production of peroxides is retarded, irritation caused by the peroxides to the skin is prevented and the safety of the cosmetic product is excellent; (4) the quality of the cosmetic product changes less and the stability of the product is excellent; (5) because of the antibacterial activity of the N-long chain monoacylated basic amino acid, contamination of the cosmetic product by microorganisms occurs only with difficulty, unlike compositions which contain silk fibroin; (6) cosmetic compositions having compounded therein silicone oil-treated inorganic pigments are sticky and have the disadvantage that the spreadability of the cosmetic over the skin is poor, but the cosmetic composition of the present invention has a dry texture and spreads well over the skin. As such, the cosmetic composition of the present invention overcomes the problems of previous inorganic pigment containing cosmetics that have not been solved heretofore.

In still another embodiment of the invention, it has been found that the salt product obtained by the reaction of a basic amino acid with a fatty acid of 8 to 22 cabon atoms effectively modifies the surface of a powdered inorganic substance. A surface modified inorganic product is simply prepared by treating a powdered inorganic substance with the basic amino acid salt and then heating the mixture at a temperature within the range of 100° to 250° C.

Suitable basic amino acids which can be used in this invention include lysine, ornithine, and $\alpha,\gamma$-diaminobutyric acid. These basic amino acids may be used either singly or in combinations. This invention does not distinguish the basic amino acids by the question of whether the amino acids are in an optically active form or in a racemic mixture.

For use in this invention, the fatty acid is required to have from 8 to 22 carbon atoms. Concrete examples of the fatty acid satisfying this requirement include caproic acid, capric acid, lauric acid, myristic acid, palmitic acid, stearic acid, oleic acid, behenic acid, iso-stearic acid, palm oil, fatty oil, and hydrozenated tallow fatty acid.

The salient feature of this invention is the absorption of a fatty acid salt of a basic amino acid on the surface of an inorganic substance and thereafter heating the inorganic substance to a temperature in the range of 100° to 250° C. This treatment induces a dehydration amidation reaction which converts the fatty acid salt of the basic amino acid into an N-acyl basic amino acid which excels in its resistance to water and solvents and, as a result, achieves the surface effect desired. If the heating is conducted at a lower temperature than specified, the conversion of the fatty acid salt of the basic amino acid to the N-acyl basic amino group does not proceed satisfactorily. The modified organic substance obtained consequently, though improved in dispersibility in organic solvents, possesses poor resistance to water and organic solvents, suffers from loss of weatherability when compounded in a cosmetic, results in a cosmetic which, when applied to the skin, comes off by perspiration. If, on the other hand, the heating is conducted at a temperature exceeding 250° C., the fatty acid or the basic amino acid undergoes oxidative decomposition and, as a result, the effect of surface modification does not reach the expected level and the treated inorganic substance takes up color and odor. The temperature of this heating must be maintained in the range of 100° to 250° C., preferably in the range of 130° to 180° C.

Although the time required for the heat treatment varies with the temperature used and the quantity of the inorganic substance under treatment, it is in the range of 30 minutes to 5 hours, preferably two to three hours where the treatment is carried out a temperature in the range of 130° to 180° C. In this case, for the purpose of precluding the oxidative decomposition of the reactants, the heating treatments may be carried out under a vacuum in or an atmosphere of nitrogen gas.

The adsorption of the fatty acid salt of the basic amino acid by the surface of the inorganic substance may be effected by (1) adding the fatty acid salt of the basic amino acid to the inorganic substance desired to be modified and comminuting the resulting mixture in a grinder such as a ball mill, an atomizer, or a colloid mill thereby mechanochemically inducing the adsoprtion, or (2) by adding the inorganic substance to a solution of the fatty acid salt of the basic amino acid, stirring the resultant mixture, and thereafter removing the solvent either by filtration or by heating under a vacuum. The second method proves to be advantageous over that of method (1) because it permits uniform surface adsorption even when the organic substance under treatment is in a small amount.

The amount of the fatty acid salt of the basic amino acid to be used in the surface treatment under discussion should fall within the range of 0.1 to 10% by weight, preferably 0.2 to 2% by weight, based on the amount of the inorganic substance given to be modified. If the amount is less than the lower limit of the range specified, the treatment does not give an ample modification effect without entailing difficulty. If the amount exceeds the upper limit of the range, the treatment proves to be uneconomical because the excess amount added is only wasted.

The method of surface modification by this aspect of the invention can be applied extensively to various inorganic substances. Suitable examples of such inorganic substances include bentonite, talc, kaolin, diatomaceous earth, light-weight silicic anhydride, mica, calcium secondary phosphate, silica, alumina, barium sulfate, titanium dioxide, zinc oxide, yellow iron oxide, red iron oxide, black iron oxide, ultramarine, chromium oxide, calcium carbonate, ferrite, metallic powder, metallic fibers, glass fibers, and asbestos.

The inorganic substances which have been surface treated by the method of this latter embodiment of the invention can be easily dispersed in an organic medium such as a polyurethane resin, vinyl chloride-vinyl acetate copolymer, epoxy resin, phenol resin, acryl resin, polyamide resin, cellulose resin, and urea resin. When an inorganic pigment treated by conventional surface modification techniques is used in paints, for example, it is frequently observed that the modifier adsorbed on the surface of the inorganic pigment dissolves out into the organic solvent to induce coagulation and separation of the inorganic pigment and impair the smooth surface and even color of the produced coats. In contrast, the inorganic pigments whose surfaces have been modified by the method of the present invention have the advantage that they exhibit excellent resistance to solvents, induce coagulation and separation only sparingly in various organic solvents including ketones such as methylethyl ketone, methylisobutyl ketone, and cyclohexanone; esters such as ethyl acetate; and hydrocarbons such as toluene and normal paraffin, and rarely impair the quality of paints.

The inorganic substances modified by this latter embodiment of the invention possess improved water repellency and adhesiveness to the skin and sparingly cause exfoliation of applied coats of makeup. Moreover, the modified inorganic substance has a smooth touch and exhibits repressed surface activity as compared with the inorganic substances not treated by the method of the present invention. Thus, they manifest outstanding qualities when used in cosmetics. As described above, the inorganic substances which have received surface modification by the latter method of the present invention can be applied to commercial production of paints and resins and to the manufacture of cosmetics.

Having generally described this invention, a further understanding can be obtained by reference to certain specific examples which are provided herein for purposes of illustration only and are not intended to be limiting unless otherwise specified.

EXAMPLE 1: Face Powder

| | |
|---|---|
| $N^\alpha$—Octanoyl-L-lysine | 35.0 wt % |
| $N^\epsilon$—palmitoyl-L-lysine | 30.0 |
| $N^\alpha$—$N^\epsilon$—dilauroyl-L-lysine | 35.0 |
| Perfumes | suitable |

The face powder having the above composition is prepared by mixing the ingredients in a ball mill. The product is very mild and safe for the human skin. It has good spreading properties over the skin and exhibits good adhesion to the skin.

EXAMPLE 2: Face Powder

| | |
|---|---|
| $N^\epsilon$—lauroyl-L-lysine | 40.0 wt % |
| Talc | 43.0 |
| Kaolin | 10.0 |
| $CaCO_3$ (Precipitated) | 2.0 |
| ZnO | 2.0 |
| Zn—stearate | 2.0 |
| $CaCO_3$ | 1.0 |
| Pigment | suitable |
| Perfumes | suitable |

The face powder having the above composition is prepared by mixing the ingredients in a ball mill. The product is very mild and safe for the human skin. It has good adhesion properties to the skin and good absorptive properties to liquid secretions.

EXAMPLE 3: Face Paste

| | |
|---|---|
| $N^\epsilon$—cocoyl-L-lysine (more than 200 mesh) | 40.0 wt % |
| Nylon 12 | 20.0 |
| Glycerin | 10.0 |
| Sodium-DL-pyrrolidone carboxylate | 3.0 |
| Pure water | 27.0 |
| Pigment | suitable |

The face paste having the above composition is prepared by mixing the ingredient in a ball mill. The product exhibits good spreading properties. It also exhibits good toilet maintenance properties.

EXAMPLE 4: Solid Face Powder

| | |
|---|---|
| $N^\alpha$—stearoyl-L-lysine | 20.0 wt % |
| $N^\epsilon$—stearoyl-L-lysine | 20.0 |
| $N^\alpha$—$N^\epsilon$—distearoyl-L-lysine | 10.0 |
| Talc | 10.0 |
| ZnO | 10.0 |
| Kaolin | 10.0 |
| Zn—stearate | 5.0 |
| $MgCO_3$ | 5.0 |
| Tragant gum aqueous soln. (as binder) | 7.0 |
| Sodium DL-pyrrolidone carboxylate | 3.0 |
| Pigment, Perfumes | suitable |

The solid face powder having the above composition is prepared by press-molding after mixing the above inorganic materials with N-acyl-lysine compounds. The product provides a comfortable and soft feel to the skin.

EXAMPLE 5: Eye Shadow

| | |
|---|---|
| $N^\epsilon$—stearoyl-L-lysine (more than 200 mesh) | 8.0 wt % |
| Talc | 1.0 |
| Pigment | 12.0 |
| Peal pigment | 18.0 |
| White Vaseline | 12.0 |
| Micro crystalline wax | 15.0 |
| Lanolin derivative | 5.0 |
| Squalane | 2.0 |
| Liquid paraffin | 27.0 |

The eye shadow having the above composition is prepared by mixing the ingredients with an emulsifier. The product had the properties of good spreadability over the skin and adhesion to the skin. It also exhibits toilet maintenance properties.

EXAMPLE 6

In several of the ketone, ester and hydrocarbon solvents described below, a stated amount of $N^\epsilon$-lauroyl-L-lysine and 1 g of an inorganic filler were shaken at 25° C. for two hours. The decrease in the amount of $N^\epsilon$-lauroyl-L-lysine in the solvent which results from the shaking treatment was determined by the absorbance at 210 nm and reported as the amount of the compound adsorbed per g of the inorganic filler.

It is noted from Table 1 that the amount of adsorption of $N^\epsilon$-lauroyl-L-lysine on various inorganic fillers substantially reached the saturation value at an extremely low application rate of about 12.50 mg. It is also noted that addition of a small amount of water, a non-solvent, promoted the adsorption and enabled further reduction of the application rate.

The inorganic fillers treated by the method described above invariably showed a critical surface tension of about 30 dynes/cm, indicating that the surface affinity for water was sufficiently repressed.

To these inorganic fillers, the $N^\epsilon$-lauroyl-L-lysine exhibited very high adsorptive strength. This critical surface tension showed no discernible change after the inorganic fillers were boiled in toluene for 10 minutes.

TABLE I

| Solvent (1) | Ethanol | 25.00 g |
|---|---|---|
| | $CaCl_2$ | 0.50 g |
| Solvent (2) | Ethanol | 23.75 g |
| | water | 1.25 g |
| | $CaCl_2$ | 0.50 g |

Absorption of the surface modifier to the inorganic materials

| Inorganic materials | Solvent | Volume of $N^\epsilon$—lauroyl-L-lysine (mg) | | | | | |
|---|---|---|---|---|---|---|---|
| | | 6.25 | 12.50 | 18.75 | 25.00 | 31.25 | 37.50 |
| $CaCO_3$ | (1) | 1.5 | 2.7 | 3.2 | 3.4 | 3.5 | 3.5 |
| | (2) | 2.0 | 3.9 | 4.5 | 4.8 | 4.8 | 5.1 |
| $\alpha$-$Fe_2O_3$ | (1) | 3.6 | 4.5 | 4.5 | 4.5 | 3.5 | 3.1 |
| | (2) | — | — | — | — | — | — |
| $TiO_2$ | (1) | 2.7 | 3.3 | 3.6 | 4.3 | 4.6 | 5.0 |
| | (2) | 4.6 | 7.3 | 8.0 | 8.6 | 9.6 | 10.6 |

EXAMPLE 7

In a container holding 25 ml of an organic solvent shown in the following table, 0.05 g of a varying surface modifier and 0.5 g of an inorganic filler were shaken on an ultrasonic shaker for 10 minutes. The container was then left standing in an erect position and placed under visual observation to rate the condition of dispersion of the inorganic filler. The rating was made on the three-point scale, wherein the circle O denotes uniform dispersion, the triangle Δ partial coagulation and separation, and the cross X represents thorough separation.

It is noted from the results of tests presented in Table 2 through Table 5 that the surface modifier of this invention excellently dispersed inorganic fillers in various organic solvents and showed no discrimination in the selection of inorganic fillers by type.

TABLE 2

Dispersion of the inorganic materials in dichloroethane

| Surface Modifier | Inorganic Materials | | | |
|---|---|---|---|---|
| | $CaCO_3$ | $Mg(OH)_2$ | $SiO_2$ | $\gamma$-$Fe_2O_3$ |
| untreated | X | X | X | X |
| stearic acid | O | Δ | Δ | Δ |
| AOT | O | O | O | X |
| Example (1) | O | O | O | O |
| (2) | O | O | O | O |

TABLE 2-continued

Dispersion of the inorganic materials in dichloroethane

| Surface Modifier | Inorganic Materials | | | |
|---|---|---|---|---|
| | $CaCO_3$ | $Mg(OH)_2$ | $SiO_2$ | $\gamma\text{-}Fe_2O_3$ |
| (3) | O | O | O | O |

TABLE 3

Dispersion of the inorganic materials in n-decane

| Surface Modifier | Inorganic Materials | | | |
|---|---|---|---|---|
| | $CaCO_3$ | $Mg(OH)_2$ | $SiO_2$ | $\gamma\text{-}Fe_2O_3$ |
| untreated | X | X | X | X |
| stearic acid | Δ | O | X | X |
| AOT | O | Δ | Δ | Δ |
| Example (4) | O | O | O | O |
| (5) | O | O | Δ | O |

TABLE 4

Dispersion of the inorganic materials in DBP

| Surface Modifier | Inorganic Materials | | | |
|---|---|---|---|---|
| | $CaCO_3$ | $Mg(OH)_2$ | $SiO_2$ | $\gamma\text{-}Fe_2O_3$ |
| untreated | O | X | O | O |
| stearic acid | O | Δ | O | O |
| AOT | O | O | X | X |
| Example (6) | O | O | Δ | O |
| (7) | Δ | O | O | O |

TABLE 5

Dispersion of the inorganic materials in toluene

| Surface Modifier | Inorganic Materials | | | |
|---|---|---|---|---|
| | $CaCO_3$ | $Mg(OH)_2$ | $SiO_2$ | $\gamma\text{-}Fe_2O_3$ |
| untreated | X | X | X | X |
| stearic acid | X | X | X | X |
| AOT | O | O | O | O |
| Example (8) | O | O | O | O |
| (9) | O | O | O | O |
| (10) | O | O | O | O |

AOT in the tables above indicates sodium dialkylsulphosuccinate which was obtained from the Kao Atlas Co., Ltd.

Lysine derivatives

EXAMPLE (1) $N^\alpha$-lauroyl-L-lysine
(2) $N^\epsilon$-stearoyl-L-lysine
(3) $N^\alpha\text{-}N^\epsilon$-dilauroyl-L-lysine
(4) $N^\alpha$-oleoyl-L-lysine
(5) $N^\alpha$-cocoyl-L-lysine
(6) $N^\epsilon$-stearoyl-L-lysine
(7) $N^\alpha$-stearoyl-$N^\epsilon$-lauroyl-L-lysine
(8) $N^\epsilon$-stearoyl-L-lysine:stearic acid (1:1 mixture)
(9) $N^\epsilon$-stearoyl-L-lysine
(10) $N^\alpha$-cocoyl-L-lysine

EXAMPLE 8: Eye Shadow

| | | |
|---|---|---|
| A: | Chromium oxide | 20 parts by weight |
| | Mica coated with bismuth oxychloride | 20 parts by weight |
| | Talc | 25 parts by weight |
| | Sericite | 15 parts by weight |
| B: | Squalane | 10 parts by weight |
| | Lanoline | 7 parts by weight |

To Component A, 3 parts by weight of a mixture of $N^\alpha$-palmitoyl-L-lysine and $N^\alpha$-cocoyl-L-arginine (weight ratio 1:1) having an average particle size of 2μ were added and the mixture was agitated for 10 minutes with a Hensil mixer to effect the surface treatment.

To the surface-treated Component A, Component B was added. After agitating and mixing the mixture with a Hensil mixer, the inner temperature of which was kept at 60° C., for 15 minutes, the mixture was cooled to 40° C. and withdrawn. The mixture was molded to prepare the product. The product showed homogeneous compatibility of the inorganic pigment of Component A with Component B and a smooth textured product without exhibiting a gritty texture was achieved upon application.

Next, 1 g of this product was spread over a Petri dish having a diameter of 4 cm, which was exposed to a xenon lamp (Xenon Tester XF-60S, made by Shimazu) for 2 hours from a distance of 1 m. The insoluble matters were dissolved out with n-hexane and the amount of peroxides produced in the solute was determined. The peroxide value of the product after exposure to the xenon lamp was 6.5. For purpose of comparison, Component A was treated with 3 parts by weight of magnesium stearate and an eye shadow was prepared which was exposed to a xenon lamp under the same conditions and the amount of peroxides produced was determined. The peroxide value after exposure was 17.7. As such, the formation of peroxides is substantially retarded in the eye shadow embodiment of the present invention which makes it a very safe product.

EXAMPLE 9: Face Powder

In 2500 g of ethanol, 50 g of calcium chloride and 2.5 g of $N^\epsilon$-lauroylLlysine were dissolved in the solution. To the solution, a mixture of 80 g of talc and 5 g of zinc flower was added and the mixture was stirred for 2 hours at room temperature. The mixture of talc and zinc flower was removed by filtration. After thoroughly washing the mixture with water to remove calcium chloride, drying was performed at 80° C. overnight under reduced pressure. $N^\epsilon$-lauroyl-L-lysine remained in the filtrate and the washing liquid was quantitatively assayed by liquid chromatography. As a result, the amount of N-lauroyl-L-lysine adsorbed by the mixture of talc and zinc flower was 0.35 g. Using the thus treated talc and zinc flower, a powder having the following composition was prepared.

| | | |
|---|---|---|
| A. | Talc treated with $N^\epsilon$—lauroyl-L-lysine | 80 parts by weight |
| B. | Zinc flower treated with $N^\epsilon$—lauroyl-L-lysine | 5 parts by weight |
| | Potato starch | 5 parts by weight |
| | Zinc stearate | 3 parts by weight |
| | Perfumes | 0.1 parts by weight |

For purposes of comparison, powders having the above composition were prepared except that untreated talc and untreated zinc flower were used instead of A and B, respectively. The powders were evaluated by 15 females over an age range of 20 to 40. The following results were obtained.

| | Prefer the powder of this invention | Prefer the powder for comparison | Hard to say which |
|---|---|---|---|
| Adherence under ordinary conditions | 9 | 2 | 4 |

-continued

|  | Prefer the powder of this invention | Prefer the powder for comparison | Hard to say which |
|---|---|---|---|
| Adherence while sweating | 12 | 0 | 3 |

(Numerals indicate the number of females who gave reply)

From the results described above, it can be understood that the powder of the present invention exhibits excellent adherency to the skin which adherency is well maintained while sweating.

EXAMPLE 10: Solid Foundation

| A: | Iron oxide yellow | 0.8 parts by weight |
|---|---|---|
|  | Indian red | 0.5 parts by weight |
|  | Titanium oxide | 11.0 parts by weight |
|  | Zinc oxide | 8.5 parts by weight |
|  | Talc | 25.0 parts by weight |
|  | Kaolin | 41.5 parts by weight |
| B: | $N^\alpha$—Cocoyl-L-ornithine (average particle size, 2μ) | 1.0 parts by weight |
|  | $N^\alpha$—Stearoyl-L-histidine (average particle size, 3μ) | 2.5 parts by weight |
| C: | Liquid paraffin | 6.0 parts by weight |
|  | 1,3-Butyleneglycol | 3.0 parts by weight |
|  | Perfumes | 0.2 parts by weight |

Component A was mixed for 10 minutes using a Hensil mixer and Component B was added thereto followed by stirring and mixture for further 10 minutes, whereby the surface treatment was effected.

Component C was added to the surface-treated Component A. After mixing and stirring the mixture for 20 minutes, the perfumes were added thereto at temperatures lower than 35° C. Stirring was performed for an additional 10 minutes. After withdrawing the mixture, it was subjected to press molding to prepare a solid foundation. The product was homogeneous and nonsticky and had smooth texture. When the product was applied to the skin, spreading over the skin was good and adherence to the skin was good.

EXAMPLE 11

(A) Preparation of sample

In 100 g of a methanol 1% lysine laurate solution, 100 g of titanium dioxide (Sample 1) was stirred for 10 minutes. The resultant solution was heated under a vacuum to expel methanol and cause the surface of titanium dioxide to adsorb lysine laurate (Sample 2). In an atmosphere of nitrogen, Sample 2 was heated at 160° C. for two hours to prepare modified titanium dioxide (Sample 3). Then, Sample 2 and Sample 3 were each stirred and washed in a 1:1 water/methanol solution (60° C.) 100 times as large in volume as each sample and then dried under vacuum to produce Samples 4 and 5, respectively.

(B) Dispersibility

Figure 1:
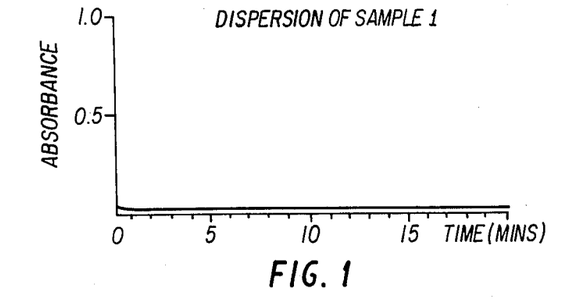
FIGS. 1 to 5 show the dispersive power of the modified surface inorganic powders of Samples 1–5 respectively of Example 12 in toluene.
Figure 2:
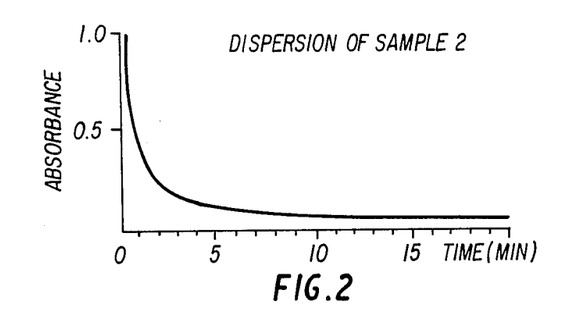
Figure 3:
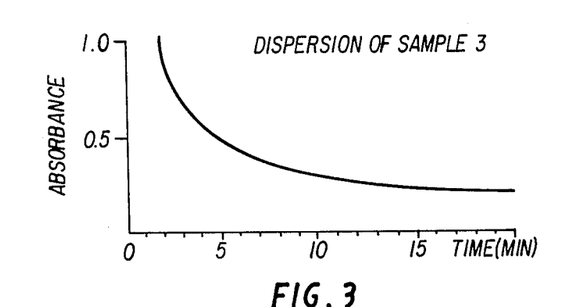
Figure 4:
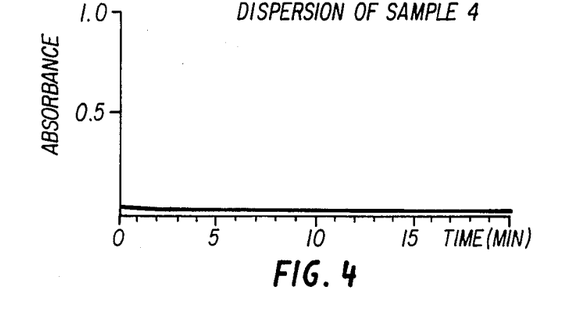
Figure 5:
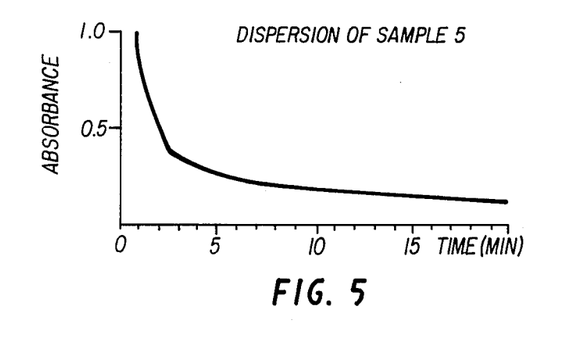

Each of the samples, Samples 1–5, was added to toluene in a concentration of 0.2% and exposed to agitating ultrasonic waves for dispersal of the inorganic substance. Each resultant dispersion was placed in a cell and subjected to an accelaration 3 times gravitational acceleration to induce forced precipitation. The stability of each dispersion was found based on the time-course change of the absorbance of the dispersion. The results are shown in FIGS. 1 through 5 respectively.

It is noted from the results of FIGS. 1 through 5 that the titanium dioxide modified by the latter surface treatment technique of the present invention exhibited a notably enhanced dispersibility in toluene and, even after washing with the water-methanol solution at 60° C., retained this effect intact. Thus, it was shown to possess outstanding resistance to water and solvents.

(C) Determination

The product on the surface of sample 5 was extracted with 100 ml of acetic acid and analyzed by High Performance Liquid Chromatography. By a comparison with standard substances, it was identified as $N^\epsilon$-lauroyl-L-lysine.

| Conditions of analysis: |
|---|
| Column: YMC-PACK-A-311, 100 mm × 6 mm Diam. (Yamamura Chemical Laboratory) |
| Eluent: 0.1 M $NaH_2PO_4$/MeOH (2/8) |
| Wavenglth: 210 nm |
| Flow volume 1.0 ml/min |

EXAMPLE 12

(A) Preparation of sample

In 100 g of a methanol 1% lysine palmitate solution, 100 g of kaolin (Sample 6) was stirred for 10 minutes. The resultant solution was heated under a vacuum to expel methanol and cause the surface of kaolin to adsorb lysine palmitate (Sample 7). In an atmosphere of nitrogen, Sample 7 was heated at 160° C. for two hours and to prepare modified kaolin (Sample 8). Then, Samples 7 and 8 were each stirred and washed in a 1:1 water/methanol solution (60° C.) 100 times as much in volume as the sample and dried under a vacuum to obtain Samples 9 and 10 respectively.

(B) Dispersibility

Figure 6:
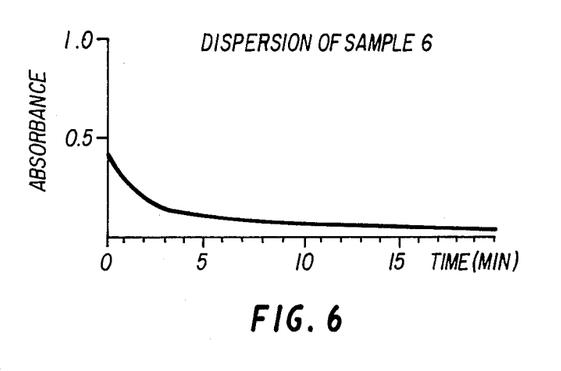
FIGS. 6 to 10 show the dispersive power of the modified surface inorganic powders of samples 6–10 respectively of Example 13 in liquid paraffin.
Figure 7:
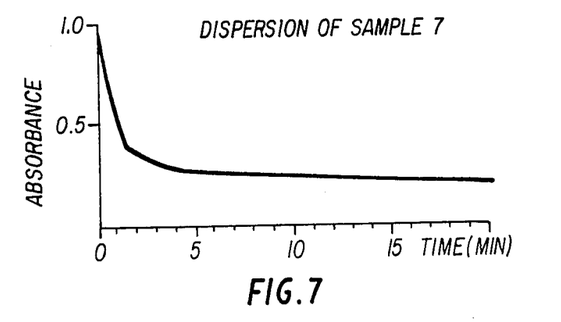
Figure 8:
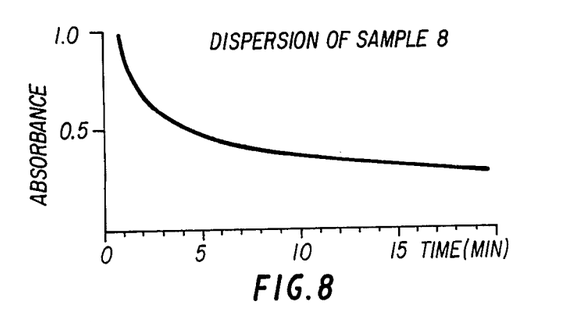
Figure 9:
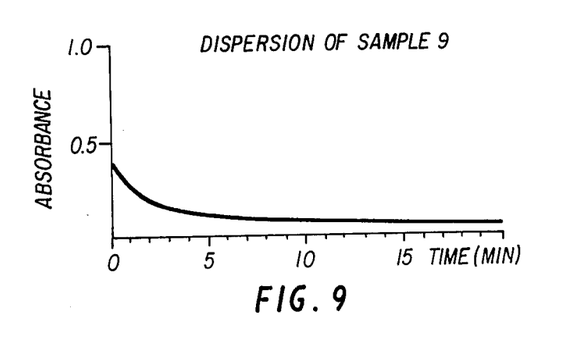
Figure 10:
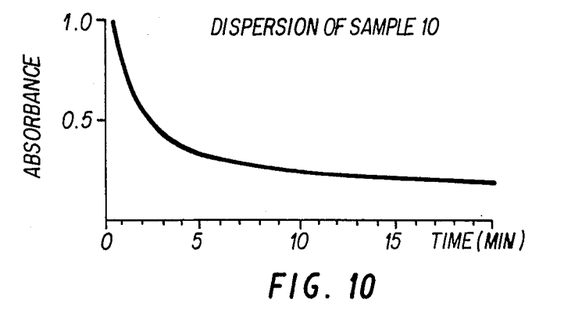

Each of Samples 6–10 was added in a concentration of 0.2% to liquid paraffin and mixed and dispersed by exposure to ultrasonic waves. The disperion was placed in a cell and subjected to an acceleration 3 times gravitational acceleration to induce forced precipitation. The stability of each dispersion was determined based on the time-course change of the absorbance. The results are shown in FIG. 6 through FIG. 10 respectively.

It is noted from the results of FIG. 6 through FIG. 10 that the kaolin treated by the latter surface modification technique of the present invention acquired notably enhanced dispersibility in liquid paraffin and, even after washing in the water-methanol solution at 60° C., retained this effect intact. Thus, it was shown to possess outstanding resistance to water and solvents.

EXAMPLE 13

(A) Preparation of sample

In 100 g of a methanol solution of 1% ornithine salt of palm oil fatty acid, 100 g of talc (Sample 11) was stirred for 10 minutes. The resultant solution was heated under a vacuum to expel methanol and cause the surface of talc to adsorb the ornithine salt of palm oil fatty acid (Sample 12). In an atmosphere of nitrogen gas, Sample 12 was heated at 160° C. for two hours to prepare improved talc (Sample 13). Then, Samples 12 and 13 were each stirred and washed in a 1:1 water-methanol solution (60° C.) 100 times as much in volume as the sample and dried under a vacuum to produce Samples 14 and 15 respectively.

(B) Dispersibility

Figure 11:
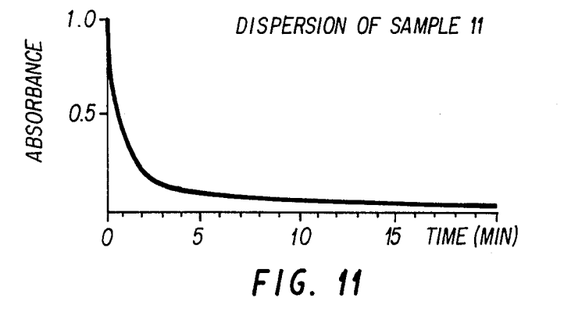
FIGS. 11 to 15 show the dispersive power of the modified surface inorganic powders of Samples 11–15 respectively of Example 15 in liquid paraffin.
Figure 12:
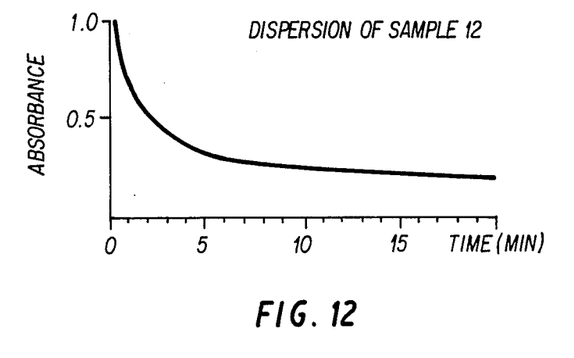
Figure 13:
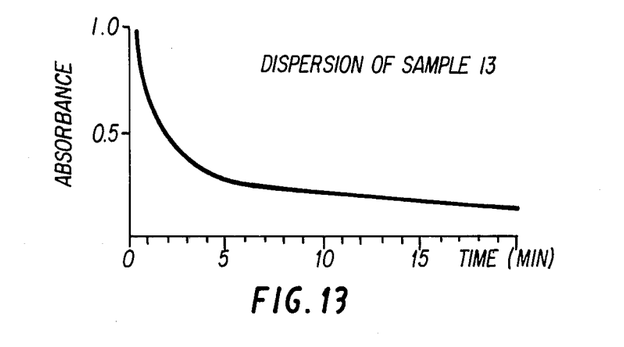
Figure 14:
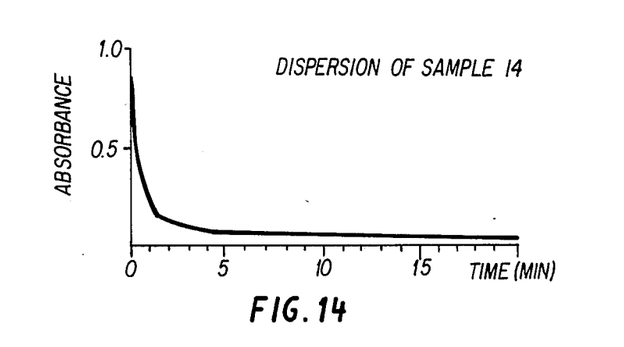
Figure 15:
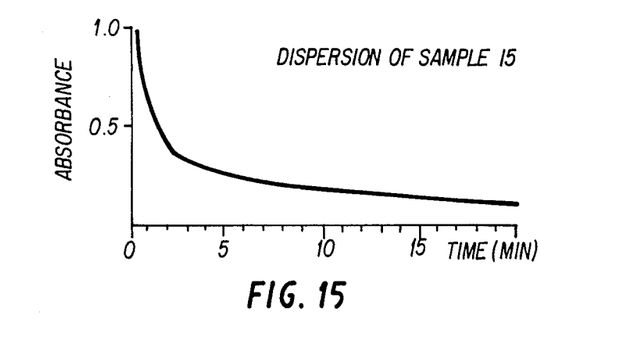

Each of the samples was added in a concentration of 0.2% to liquid paraffin and mixed and dispersed by exposure to ultrasonic waves. This dispersion was placed in a cell and subjected to an acceleration 3 times gravitational acceleration to induce forced precipitation. The stability of each dispersion was determined based on the time-course change of the absorbancy. The results are shown in FIG. 11 through FIG. 15 respectively.

It is noted from the results of FIG. 11 through FIG. 15 that the talc treated by the latter surface modification technique of the present invention acquired notably enhanced dispersibility in liquid paraffin and, even after washing in the water-methanol solution at 60° C., retained its effect intact. Thus, it was shown to possess outstanding resistance to water and solvents.

EXAMPLE 14

Each of the samples shown below was placed in the amount of 0.5 g in a container holding 25 ml of a given organic solvent indicated in the following table. Each container was shaken on an ultrasonic shaker for 10 minutes. It was then left standing at rest in an errect position and kept under visual observation to determine the condition of each dispersed sample.

The Experimental results obtained showing the dispersive force of the inorganic powder on which the surface is treated with the surface modifiers are shown in Tables 6-8.

The results indicate that the treated inorganic powders are well dispersed in each organic solvent.

TABLE 6: Dispersion in dichloroethane

Sample 1 in example 11: not good
Sample 6 in example 12: not good
Sample 11 in example 13: not good
Sample 3 in example 11: good
Sample 8 in example 12: good
Sample 13 in example 13: good TABLE 7: Dispersion in n-decane Sample 1 in example 11: not good
Sample 6 in example 12: not good
Sample 11 in example 13: not good
Sample 3 in example 11: good
Sample 8 in example 12: good
Sample 13 in example 13: good TABLE 8: Dispersion in dibutyl phthalate Sample 1 in example 11: not good
Sample 6 in example 12: not good
Sample 11 in example 13: not good
Sample 3 in example 11: good
Sample 8 in example 12: good
Sample 13 in example 13: good Cosmetic compositions prepared from specific samples of surface modified inorganic powders are shown below.

EXAMPLE 15: Face powder

| | |
|---|---|
| Sample 3 in example 11 | 35.0 wt % |
| Sample 8 in example 12 | 30.0 |
| Sample 13 in example 13 | 35.0 |
| Pigment | suitable |
| Perfumes | suitable |

Samples of surface modified inorganic powders taken from Samples 3, 8 and 13, were prepared by washing each sample with methanol followed by drying. Face powders containing the surface modified powders as shown above were prepared by mixing the ingredients in a ball mill. The products were very mild and safe for the human skin. They had the properties of good spreadability characteristics over the skin and good adhesion to the skin.

EXAMPLE 16: Face paste

| | |
|---|---|
| Sample 3 in example 11 (more than 200 mesh) | 10.0 wt % |
| Sample 8 in example 12 | 15.0 |
| Sample 13 in example 13 | 35.0 |
| Glycerin | 10.0 |
| Sodium DL-pyrrolidone carboxylate | 3.0 |
| Liquid paraffin | 27.0 |
| Pigment, Perfumes | suitable |

Samples of surface modified inorganic powders taken from Samples 3, 8 and 13, were prepared by washing with methanol and drying. Face pastes having the above composition were prepared by mixing the ingredients with emulsifier. The product had the properties of good spreadability over the skin and adheasion to the skin. They also had good toilet maintenance characteristics.

EXAMPLE 17: Solid face powder

| | |
|---|---|
| Sample 3 in example 11 (more than 200 mesh) | 20.0 wt % |
| Sample 8 in example 12 | 30.0 |
| Sample 13 in example 13 | 30.0 |
| Zn—stearate | 5.0 |
| $MgCO_3$ | 5.0 |
| Tragant gum aqueous soln. | 7.0 |
| Sodium-DL-pyrrolidone carboxylate | 3.0 |
| Pigment | suitable |
| Perfumes | suitable |

Samples of surface modified inorganic powder taken from Samples 3, 8 and 13, was prepared by washing with methanol and drying. Solid face powders of the above compositions were prepared by press-molding after mixing the above materials. The products obtained exhibited a comfortable and soft feel to the skin.

EXAMPLE 18: Eye shadow

| | |
|---|---|
| Sample 3 in example 12 (more than 200 mesh) | 9.0 wt % |
| Pigment | 12.0 |
| Peal pigment | 18.0 |
| White Vaseline | 12.0 |
| Lanolin derivative | 5.0 |
| Micro crystalline wax | 15.0 |
| Squalane | 2.0 |
| Liquid paraffine | 27.0 |

A sample of surface modified inorganic powder taken from Sample 3 was prepared by washing it with methanol and drying. The eye-shadow product having the above composition was prepared by press-molding after mixing the above materials with an emulsifier apparatus. The product provides a comfortable and soft feel to the skin.

EXAMPLE 19

The peroxide values of olive oil examined in conjunction with Samples 1, 2 and 3, are shown below. Olive oil containing solutions were prepared by combining 25 ml of olive oil with surface modified powder obtained from Samples 1, 2 or 3 from Example 11 and heating each dispersion to 98° C. with blown air. After 30 hrs. of heating, the peroxide value of olive oil was determined.

|  | The peroxide value (POV) |
|---|---|
| Sample 1 in example 11 | 160 |
| Sample 2 in example 11 | 45 |
| Sample 3 in example 11 | 7 |

It is clear from the results of this experiment that titanium dioxide treated with the latter surface modifier of the present invention had its surface activity suppressed by the modifier. The modified $TiO_2$ did not accelerate the decomposition of oil surrounding it and hardly any unsafe peroxide (unsafe to the skin) was found in the olive oil. It is concluded from the experiments described above that the modifiers and surface modified inorganic materials are safe and that they have the ability to suppress the decomposition of the base oil surrounding the inorganic particles.

Having now fully described the invention, it will be apparent to one of ordinary skill in the art that many changes and modifications can be made thereto without departing from the spirit or scope of the invention as set forth herein.

What we claim is:

1. An inorganic composition of improved characteristics, comprising:
   at least one particulate inorganic substance whose surface is modified by an N-acylated lysine.

2. The composition of claim 1, which comprises said surface modified inorganic substance in a paint formulation or a resin formulation.

3. The composition of claim 2, wherein said inorganic substance is calcium carbonate, titanium dioxide, kaolin, talc, silica, ferrite, chromium dioxide, metallic fibers, glass fibers or asbestos.

4. The composition of claim 2, wherein said N-acylated basic amino acid is at least one N-acyl lysine of the formula:

wherein the RCO group represents an aliphatic acyl radical of 8 to 22 carbon atoms and the R'CO and R"CO groups each represent an aliphatic acyl radical of 1 to 22 carbon atoms with the proviso that the two aliphatic acyl groups jointly have from 9 to 44 carbon atoms.

5. The composition of claim 4, wherein said N-acylated basic amino acid is $N^\alpha$-octanoyl-lysine, $N^\alpha$-oleoyl-lysine, $N^\alpha$-lauroyl-lysine, $N^\alpha$-myristoyl-lysine, $N^\alpha$-palmitoyl-lysine, $N^\alpha$-stearoyl-lysine, $N^\epsilon$-octanoyl-lysine, $N^\epsilon$-oleoyl-lysine, $N^\epsilon$-lauroyl-lysine, $N^\epsilon$-myristoyl-lysine, $N^\epsilon$-palmitoyl-lysine, $N^\epsilon$-stearoyl-lysine, $N^\alpha$-lauroyl-$N^\epsilon$-stearoyl-lysine, $N^\alpha$-hexanoyl-$N^\epsilon$-palmitoyl-lysine, $N^\alpha$-$N^\epsilon$-dilauroyl-lysine or mixtures thereof.

6. The composition of claim 2, which further comprises said surface modified inorganic substance in a cosmetic formulation.

7. The composition of claim 6, wherein said particulate inorganic substrate is an inorganic pigment selected from the group consisting of talc, kaolin, zinc oxide, diatomaceous earth, light weight silicic anhydride, mica, calcium secondary phosphate, silica, alumina, barium sulfate, titanium dioxide, yellow iron oxide, black iron oxide, red iron oxide, ultramarine, chromium hydroxide, chromium oxide, calcium carbonate, montomorillonite titanium coated-mica, silicic acid, Prussian blue, zinc flowers, clay, and precipitated calcium carbonate.

8. The composition of claim 6, wherein said N-acylated lysine is a N-monoacylated lysine acylated with an aliphatic acyl group of 8 to 22 carbon atoms.

9. The composition of claim 8, wherein said N-monoacylated basic amino acid is $N^\epsilon$-2-ethyl-hexanoyl-lysine, $N^\epsilon$-lauroyl-lysine, $N^\epsilon$-cocoyl-lysine, $N^\epsilon$-palmitoyl-lysine, $N^\epsilon$-isostearoyl-lysine, $N^\epsilon$-hydrogenated tallow fatty acid-acyl-lysine, $N^\alpha$-capryloyl-lysine, $N^\alpha$-lauroyl-lysine, $N^\alpha$-myristoyl-lysine, $N^\alpha$-oleoyl-lysine, $N^\alpha$-behenoyl-lysine.

10. The composition of claim 8, wherein said N-acylated lysine is an N, N-diacyl-lysine with each aliphatic acyl group of 1 to 22 carbon atoms with the proviso that the two aliphatic acyl groups jointly have from 9 to 44 carbon atoms.

11. The composition of claim 10, wherein said N,N-diacyl-lysine is $N^\alpha$, $N^\epsilon$-diacyl-lysine, $N^\alpha$-lauroyl-$N^\epsilon$-stearoyl-lysine, $N^\alpha$-hexanoyl-$N^\epsilon$-palmitoyl-lysine, $N^\alpha$, $N^\epsilon$-dilauroyl-lysine, $N^\epsilon$-lauroyl-$N^\alpha$-acetyl-lysine, $N^\alpha$, $N^\epsilon$-dipalmitoyl-lysine $N^\alpha$, $N^\epsilon$-distearoyl-lysine or the mixture thereof.

12. The composition of claim 1, wherein said surface modified inorganic substance is prepared by allowing a particulate, raw material inorganic substance to absorb a salt of a basic amino acid with a fatty acid of 6 to 22 carbon atoms, and subsequently heating the substance to a temperature within the range of 100° to 250° C.

13. The composition of claim 12, wherein the temperature of said heating step ranges from 130° C. to 180° C.

14. The composition of claim 12, wherein said fatty acid is caproic acid, caprylic acid, capric acid, lauric acid, myristic acid, palmitic acid, stearic acid, oleic acid, behenic acid, isostearic acid, cocoyl fatty acid, palm oil fatty acid or hydrogenated beef tallow fatty acid.

15. The composition of claim 12, wherein said surface modified inorganic substance is selected from the group consisting of talc, kaolin, zinc oxide, diatomaceous earth, light weight silicilic anhydride, mica, calcium carbonate, calcium secondary phosphate, silica, alumina, balium sulfate, titanium dioxide, yellow iron oxide, red iron oxide, black iron oxide, ultramarine, chronium hydroxide, montomorillonite, titanium-coated mica, silicic acid, Prussiun blue, zinc flowers, clay, precipitated calcium carbonate.

16. The composition of claim 12, which comprises said surface modified inorganic substance in a resin formulation, a paint formulation or a cosmetic formulation.

* * * * *